US012805592B2

(12) United States Patent
Kushnirov et al.

(10) Patent No.: US 12,805,592 B2
(45) Date of Patent: Nov. 24, 2026

(54) EARMUFF UNIT FOR USE WITHIN A HEAD PROTECTIVE GEAR AND HEAD PROTECTIVE GEAR

(71) Applicant: Cardo Systems, Ltd., Ra'anana (IL)

(72) Inventors: Avram Kushnirov, Barkan (IL); Eran Lazarovich, Misgav Dov (IL); Ari Manoach, Tel-Avi (IL); Dan Emodi, Herzlia (IL)

(73) Assignee: Cardo Systems, Ltd., Ra'anana (IL)

( * ) Notice: Subject to any disclaimer, the term of this patent is extended or adjusted under 35 U.S.C. 154(b) by 338 days.

(21) Appl. No.: 18/573,638

(22) PCT Filed: Jun. 23, 2022

(86) PCT No.: PCT/IB2022/055816

§ 371 (c)(1),
(2) Date: Dec. 22, 2023

(87) PCT Pub. No.: WO2023/275678

PCT Pub. Date: Jan. 5, 2023

(65) Prior Publication Data

US 2024/0298733 A1 Sep. 12, 2024

Related U.S. Application Data

(60) Provisional application No. 63/216,857, filed on Jun. 30, 2021.

(51) Int. Cl.
*A42B 3/16* (2006.01)
*A61F 11/14* (2006.01)
(Continued)

(52) U.S. Cl.
CPC .............. *A42B 3/166* (2013.01); *A61F 11/14* (2013.01); *H04R 1/023* (2013.01); *H04R 1/1008* (2013.01);
(Continued)

(58) Field of Classification Search
CPC .. A42B 3/166; A42B 3/04; A42B 3/16; A42B 3/306; A61F 11/14; H04R 1/023;
(Continued)

(56) References Cited

U.S. PATENT DOCUMENTS 3,178,723 A * 4/1965 Aileo ..................... A42B 3/166 381/376
RE34,525 E * 2/1994 Lazzaroni ................ A42B 3/04 379/430
(Continued)

FOREIGN PATENT DOCUMENTS

CN 112261537 A * 1/2021 ............... H04R 3/02
JP 2000023277 A 1/2000
(Continued)

OTHER PUBLICATIONS

International Application No. PCT/IB2022/055816, International Search Report and Written Opinion mailed Jun. 23, 2022, 10 pages.

*Primary Examiner* — Angelica M Mckinney
(74) *Attorney, Agent, or Firm* — Kilpatrick Townsend & Stockton LLP

(57) ABSTRACT

An earmuff unit for use within a head protective gear. The head protective gear is separate from the earmuff unit. The earmuff unit comprises an ear pad. The earmuff unit also comprises a flexible element arranged in at least a lower portion of a circumference of the ear pad to allow the ear pad to move, in at least a part of the lower portion of the circumference, towards and away from a shell of the head protective gear.

31 Claims, 4 Drawing Sheets

(51) Int. Cl.
*H04R 1/02* (2006.01)
*H04R 1/10* (2026.01)

(52) U.S. Cl.
CPC ......... *H04R 1/1066* (2013.01); *H04R 1/1075* (2013.01); *H04R 1/1083* (2013.01)

(58) Field of Classification Search
CPC .. H04R 1/1008; H04R 1/1066; H04R 1/1075; H04R 1/1083; H04R 2201/023; H04R 5/04; H04R 3/02; G10K 11/17857
See application file for complete search history.

(56) References Cited

U.S. PATENT DOCUMENTS

| | | | | |
|---|---|---|---|---|
| 8,429,766 | B2 * | 4/2013 | Halfaker | A42B 3/166 2/209 |
| 10,104,929 | B2 * | 10/2018 | Schrader | A42B 3/166 |
| 12,010,494 | B1 * | 6/2024 | Satongar | H04R 5/04 |
| 2012/0102629 | A1 * | 5/2012 | Lott | H04R 1/1066 2/410 |
| 2016/0095376 | A1 | 4/2016 | Schrader et al. | |
| 2018/0242082 | A1 * | 8/2018 | Hua | G10K 11/17857 |
| 2023/0292035 | A1 * | 9/2023 | Khonsaripour | A42B 3/306 |

FOREIGN PATENT DOCUMENTS

| | | | | |
|---|---|---|---|---|
| WO | WO-2004089137 | A1 * | 10/2004 | A42B 3/16 |
| WO | 2007122496 | A1 | 11/2007 | |
| WO | 2008139240 | A1 | 11/2008 | |
| WO | WO-2011068407 | A1 * | 6/2011 | A42B 3/16 |

* cited by examiner

EARMUFF UNIT FOR USE WITHIN A HEAD PROTECTIVE GEAR AND HEAD PROTECTIVE GEAR

CROSS REFERENCE TO RELATED APPLICATION

This application is a U.S. national phase of International Patent Application No. PCT/IB2022/055816 filed on Jun. 23, 2022, which claims the benefit of U.S. Provisional Application No. 63/216,857, filed Jun. 30, 2021, which are herein incorporated by reference in their entireties for all purposes.

The invention relates to an earmuff unit for use within a head protective gear, said earmuff unit comprising an ear pad.

Earmuff units contribute considerably to noise reduction as they provide a close contact to the user's ear or even a closed space around the user's ear. This is not only true for proper earmuff units, i.e. earmuff units merely intended for protecting the user from noise, but also for over-the-ear headphone units and—although with lesser significance—also for on-ear headphones comprising at least one loudspeaker and providing a predefined acoustic environment allowing the loudspeaker to be operated at a lower volume. Furthermore, said predefined acoustic environment is of particular importance when applying Active Noise Cancellation (ANC) so as to further reduce the noise level.

When putting the head protective gear on or taking it off, however, at least the lower part of the ear pad may enter into contact with the user's ear which may limit the user's ability to put on the head protective gear, possibly require a special effort such as pushing elements of the head protective gear sideways with the user's fingers, which may be experienced by the user at least as unpleasant and sometimes even painful.

It is to be noted already at this point that, in the context of the present invention, the terms "lower" and "upper" refer to a state in which the user wears the earmuff unit over his/her ear. In this state, the user's earlobe forms a lower part of the user's ear, while the ear's helix is located in the ear's upper part.

In view of the above, it is the object of the present invention to provide an improved earmuff unit.

According to the present invention, this object is solved by an earmuff unit as defined at the outset, in which a flexible element is arranged in at least a lower portion of the ear pad's circumference, so as to allow the ear pad in at least a part of said lower portion to move towards and away from a shell of the head protective gear. It is to be noted that neither the shell nor the head protective gear are elements of the earmuff unit. As a consequence of the construction according to the invention, it is only the ear pad which in at least said part of said lower portion moves relative to the head of the user, in particular the user's ears. Furthermore, the head protective gear may be easily put on or taken off in a state, in which at least said lower portion of the ear pad is retracted towards the shell of the head protective gear, thus avoiding any unpleasant or even painful contact with the user's ears. Consequently, the earmuff unit according to the present invention provides, in addition to providing a general protection of the ear, e.g. from dust, insects, and the like, comfort when putting the head protective gear on or taking it off in a folded state of the flexible element as well as effective noise reduction in an expanded state of the flexible element.

US 2012/0102629 A1 discloses an over-the-ear headphone unit for use within a helmet. Said headphone unit comprises a housing rigidly supporting a speaker and an ear pad fixedly attached to the housing. An inflatable bladder formed separately from the headphone unit is located between the headphone unit and the helmet. The bladder may be inflated so as to force the headphone unit in its entirety against the user's head. The above-discussed problem encountered during the putting on and taking off of the helmet, however, is not addressed in US 2012/0102629 A1.

Furthermore, U.S. Pat. No. 8,429,766 B2 discloses an earmuff unit connected to the shell of a head protective gear via an inflatable bladder located between the earmuff unit and the shell. According to one embodiment, a chin strap of the head protective gear may be connected to the inflatable bladder. However, U.S. Pat. No. 8,429,766 B2 fails to mention the reason for this constructional detail.

It should be noted that the head protective gear generally may be of any design, as long as its shell covers the user's ears. In particular, the head protective gear may include a hard shell or a soft shell. As head protective gears including a hard shell, motorcycle helmet, sports helmets, professional protective helmets and the like are known. These helmets may be of different design. In particular, the helmet may be a full helmet, a cross helmet, a flip-up helmet, a jet helmet and the like, but not a brain cap. Head protective gears including a soft shell, for example, are used in martial arts, e.g. boxing, kickboxing and the like.

It should be noted in the context of the present invention that if the ear pad is intended to surround the ear of the user of the head protective gear, it needs not to surround the ear completely. In particular with head protective gears, e.g. motorcycle helmets, worn when driving/riding on public streets or roads, there might be a concern that ear pads completely surrounding the user's ear could limit the user's ability to hear sounds from the environment, thus causing a potential accident risk. And in different countries, this potential accident risk resulted in corresponding legal regulations. Different solutions could be envisaged in order to mitigate or even dispel such concerns. For example, sound from the environment could be recorded using an external microphone and mixed to the signal supplied to a speaker located in the ear pad. According to a further example, a hole penetrating the ear pad or cut into the ear pad could be provided, allowing sound from the environment to enter into the space surrounded by the ear pad. The position and/or dimensions and/or shape of such a hole, as well as the connection of the strap in case such hole is at the bottom part of the ear pad, may easily be adopted to the specific application of the head protective gear. For example, this hole could be located in the lower part of the ear pad and/or in the back of the ear pad. According to a still further example, a hole could be provided which penetrates not only the earmuff unit, but also the shell of the head protective gear in a substantially radial direction with respect to the user's head. Preferably, this hole can take different shapes, measures or directions or be a combination of more than one hole, all for a purpose of enabling hearing some environmental sound while lowering wind noise.

According to a first alternative, the flexible element may be a compressible element integrated in said ear pad. By compressing the compressible element the ear pad may be moved towards the shell of the head protective gear in order to allow putting the head protection gear on or off.

If said compressible element is elastically compressible, the ear pad may automatically move away from said shell of the head protective gear, i.e. to automatically return towards the head of the user of the head protective gear, after having been compressed in order to allow to pass the user's ears when putting the helmet on or off. For example, said compressible element is made from, preferably elastically, compressible foam material.

It should be noted that in the context of the present invention the term "foam material" is intended to cover also materials having a foam-like structure, e.g. natural or artificial sponges.

If said flexible element is arranged in an upper portion of the ear pad's circumference as well, putting glasses, e.g. optometric glasses, sun glasses or the like, on or off when wearing the head protective gear may be facilitated. In particular, the flexible element or its compressible element may easily yield to the pressure exerted by the glasses' temples and slip aside giving way to the temples' movement along the user's head. Furthermore, it is conceivable to provide ear pas having a depression or recess allowing the temples even easier to pass the ear pad.

In order to avoid the necessity of additional manipulation of the head protection gear or the earmuff unit, one longitudinal end of an elongate connection element may be connected to a lower end of the ear pad, while the respective other longitudinal end of said elongate connection element may be adapted to be connected to a chin strap of the head protective gear. This construction takes advantage of the fact that users of head protective gears usually grip the chin straps of the head protective gear when putting the head protective gear on or off and, when doing so, pull both chin straps sideways away from their head. Due to the ear pads being connected to the chin straps via the elongate connection elements, pulling the chin straps sideways away from the head results in a compression of the flexible element of the ear pad, thus allowing the head protective gear to easily pass the user's ears. Again it is to be noted that neither the chin strap nor the head protective gear are elements of the earmuff unit.

In order to allow to efficiently compress the flexible element, it is advantageous, if the elongate connection element is connected to an laterally inner side of the ear pad, i.e. that side of the ear pad facing towards the user's head and away from the adjacent section of the head protective gear's shell.

If said elongate connection element is elastically stretchable, wrinkling of the elongate connection element in a state in which the user wears the head protective gear may be avoided. Of course, the elongate connection element has to be rigid enough in order to effect the compression of the flexible element of the ear pad when being pulled sideways.

As the chin straps, on the one hand, have a predetermined width, and as it is advantageous, on the other hand, to connect the elongate connection element to the lower part of the ear pad over at least a predetermined length in circumferential direction of the ear pad, preferably over substantially the entire width of the ear pad, it can be advantageous, if said elongate connection element is a strip element.

In order to provide the afore-mentioned closed space around the user's ear, the earmuff unit may further comprise a housing. Via this housing, said earmuff unit may be connected to the shell of the head protective gear. The width of the elongate connection element may, for example, vary from the width of the ear pad at its one longitudinal end to the width of the chin straps at its other longitudinal end.

Furthermore, said housing may have a wedge-shaped design tapering towards a lower part thereof so as to allow the ear pad to approach the housing in the lower part of the earmuff unit, e.g. by folding the flexible element.

As already mentioned before, the earmuff unit may be designed as over-the-ear headphone unit by including at least one loudspeaker, which, for example, may be supported by said housing.

In order to simplify the design and mounting of the earmuff unit, the flexible element may extend substantially over the entire circumference of the ear pad. Accordingly, the flexible element may substantially adopt the annular shape of the ear pad, and may in particular have a substantially tubular shape.

The ear pad's movement relative to the housing may be effected by pneumatic means, e.g. by inflating/deflating a bladder using a manually or electrically operated pump, by electro-mechanical means, e.g. by using a servo-motor, or the like.

Furthermore, such pneumatic means could be used for inflating the ear pad, in particular the flexible element, in order to improve the abutment thereof against the user's head. Inflating the flexible element may be particularly advantageous, if the foam material is an open-pore foam material, preferably having a closed outer surface.

As is known from prior art headphone units, an acoustic mesh may be arranged between said housing and said ear pad.

In order to provide the headphone unit according to the present invention with active noise cancellation properties, at least one microphone may be mounted to the housing. For example, a microphone may located in front of said at least one loudspeaker. Furthermore, an additional microphone may be located behind and/or below said at least one loudspeaker.

According to a second alternative, said flexible element being arranged between said ear pad and said housing, so as to allow the ear pad in at least said part of said lower portion of the ear pad's circumference to move towards and away from said housing.

In order to provide sufficient space for all components of the earmuff unit, e.g. the at least one loudspeaker of a headphone unit, it is further suggested that, in the expanded state of the flexible element, the housing and the flexible element together form a bowl of substantially uniform height over the entire circumference.

In order to provide an improved support for the ear pad, a stabilizing ring element may be mounted between the ear pad and the flexible element.

Advantageously, at least one of the housing and the stabilizing ring element may be made from a rigid material, so as to increase the dimensional stability of the earmuff unit. Examples of suitable rigid materials are e.g. a thermoplastic material, for example, polycarbonate, ABS and the like, e.g. reinforced with fibers, preferably glass fibers.

It is, however, also conceivable that the housing may at least in part be made from a flexible material, e.g. from silicone, rubber, coated foam and the like. For example, all parts which are not required for protecting the electronics may be made of flexible material.

In order to facilitate the mounting of the flexible element, it is suggested that at least one of the housing and the stabilizing ring element has a circumferential groove intended to cooperate with a mating circumferential lip of the flexible element. Preferably, the circumferential groove opens in a radially outward direction, while the circumferential lip protrudes from the flexible element in a radially inward direction.

Furthermore, the reproducibility of the movement of the ear pad relative to the housing may be improved, if said stabilizing ring element is pivotably connected to the housing. Advantageously, the pivotable connection may be provided at an upper portion of the earmuff unit. For example, the pivotable connection may be provided by a hinge unit having a hinge axis, preferably a hinge axis extending substantially parallel to a forward-backward direction of the user's head.

In order to initiate and/or support the ear pad's movement towards the housing, e.g. by folding the flexible element, and/or away from the housing, e.g. by expanding the flexible element, a plurality of activation mechanisms are conceivable.

For example, a Bowden-like cable may be provided for at least one of moving said ear pad towards said shell and moving said ear pad away from said shell. Preferably, said Bowden-like cable may be connected to said stabilizing ring element which in turn is connected to said ear pad.

In order to avoid the necessity of separately operating the Bowden-like cable, said Bowden-like cable may be adapted to be connected to a chin strap of the head protective gear. Thus, whenever the user pulls the chin straps, e.g. when putting the head protective gear on or when loosening the chin straps connection for taking the head protective gear off, the Bowden-like cables move the ear pad towards the shell of the head protective gear.

According to a further improvement of the present invention, a latching mechanism may be provided for holding the ear pad in a retracted position, i.e. in a position moved towards the shell, which position corresponds to the folded state of the flexible element.

In order to enable the ear pad to substantially automatically return to a position remote from the shell, i.e. a position in which it abuts against the user's head, which position corresponds to the expanded state of the flexible element, a spring element may be provided for at least one of biasing said ear pad away from said shell and biasing said ear pad towards said shell. For example, said spring element may act on said stabilizing ring element.

And, in order to trigger this return movement, a button for releasing the latching mechanism may be provided. This button may be located at any suitable position of the head protective gear.

According to a second aspect, the present invention relates to a head protective gear having an outer shell and an inner padding and including at least one earmuff unit including at least one of the afore-described earmuff unit features and mounted in an allocated recess of the inner padding.

According to this second aspect, it may also be conceivable that the earmuff unit or at least a part of the earmuff unit, e.g. the ear pad, may be integrally formed with the inner padding of the head protective gear.

In order to be able to record environmental sound or noise, for example in the context of Active Noise Cancellation (ANC), a microphone or further microphone may be located outside the head protective gear.

Furthermore, independent protection is sought for the afore-described operating mechanism. Thus, the invention relates, according to a third aspect, to a head protective gear having an outer shell and an inner padding, including at least one earmuff unit mounted in an allocated recess of the inner padding, and further including at least one of a spring element for biasing said at least one earmuff unit away from said outer shell and a Bowden-like cable for retracting said at least one earmuff unit towards said outer shell.

Furthermore, the housing may be made from a plurality of elements, e.g. a main housing element and at least one of an upper cover element, e.g. allowing in a state removed from the main housing element mounting said loudspeaker in said housing, and a lower cover element, e.g. enclosing together with said main housing element a chamber including the control electronics and possibly a second microphone.

In the following, the invention will be described in more detail referring to specific embodiments. Merely for the sake of simplicity, the earmuff units shown in the drawings are designed as over-the-ear headphone units, and the head protective gear is designed as a helmet. It is to be understood, however, that this is not intended in any way to limit the scope of protection.

Figure 1:
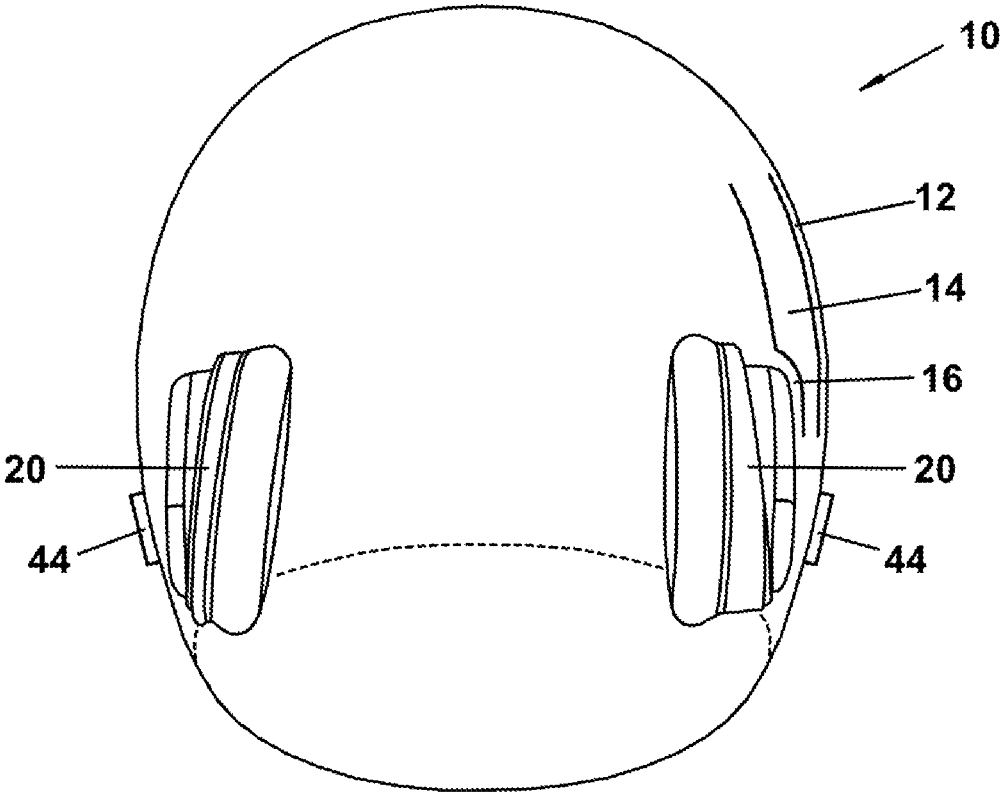
FIG. 1 shows a schematic view of a helmet including two headphone units according to the invention.

In FIG. 1 a helmet (as an example of a head protective gear) is generally denoted by reference numeral 10. The helmet 10 comprises an outer shell 12 and an inner padding 14, schematically indicated in FIG. 1. Generally, the helmet 10 may be of any design, as long as the outer shell 12 covers the user's ears. In other words, the helmet 10 may be a full helmet, a cross helmet, a flip-up helmet, a jet helmet and the like, but not a brain cap.

At the locations intended to protect the user's ears, the padding 14 has two recesses 16, which are intended to receive two earmuff units according to the present invention, in particular two foldable headphone units 20. FIG. 1 shows the left headphone unit 20 in its folded state and the right headphone unit 20 in its expanded state.

In the following the design of the headphone unit 20 will be described in more detail referring to FIGS. 2 to 6.

The headphone unit 20 comprises a housing 22 rigidly supporting a loudspeaker 24, a flexible element 26, a stabilizing ring element 28, and an ear pad 30.

The ear pad 30 is intended to surround the user's ear in a condition in which the ear pad 30 is abutting against the user's head. To this end, the ear pad 30 preferably is made from a soft resilient material, e.g. synthetic leather, a silicone gel, natural leather, foam with multiple densities and the like, or an inflatable bladder (not shown). Nevertheless, any contact between the user's ear and the ear pad 30 when putting the helmet 10 on or taking it off may be unpleasant or even painful to the user.

Figure 3:
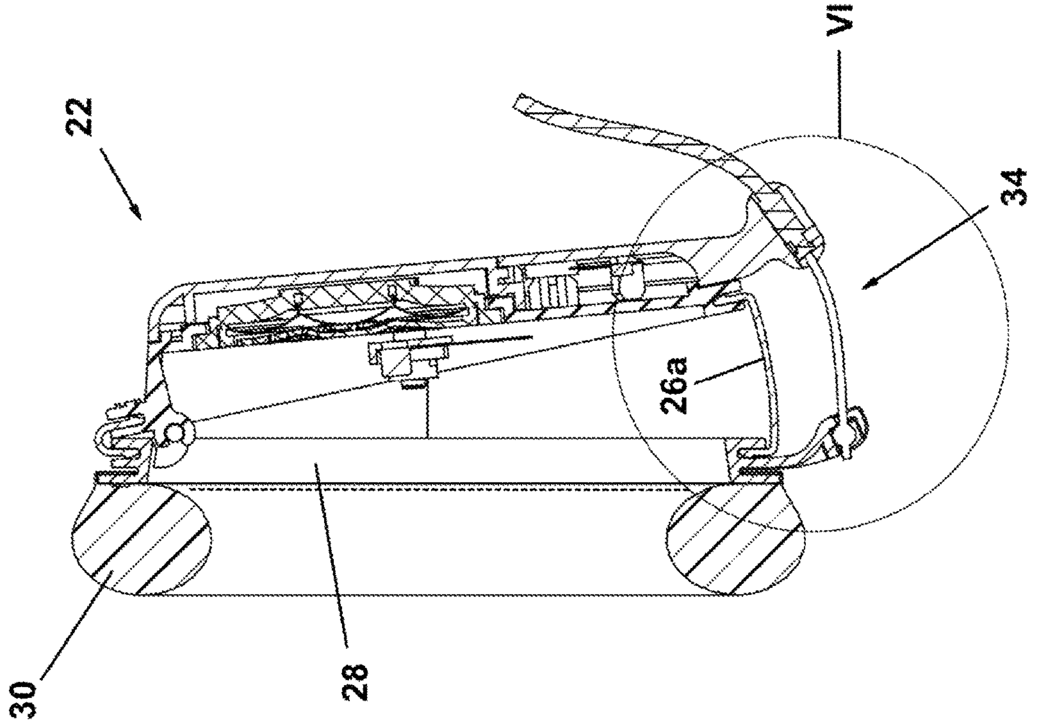
FIGS. 2 and 3 show two sectional views of the headphone unit, namely in a folded state (FIG. 2) and an expanded state (FIG. 3) of the flexible element.
Figure 2:
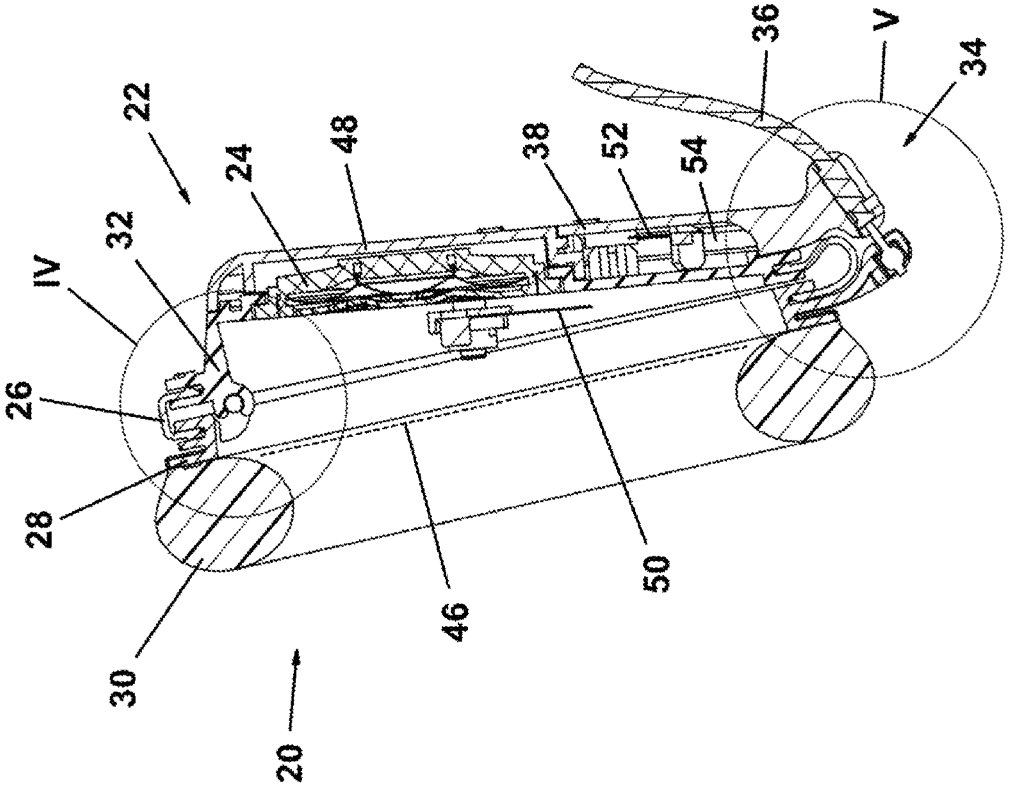
Figure 6:
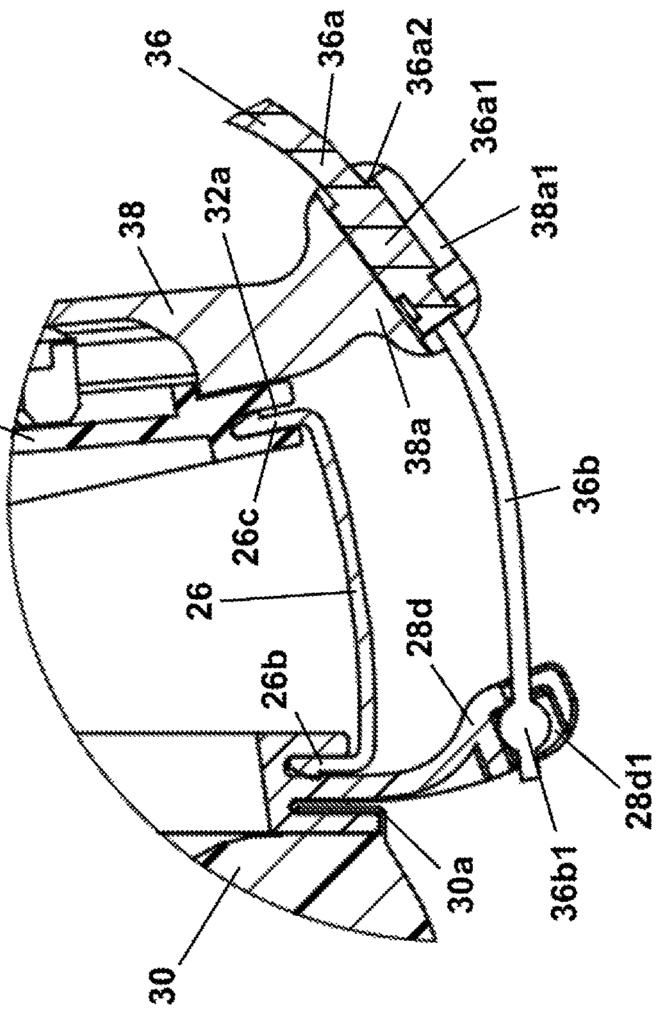
Figure 5:
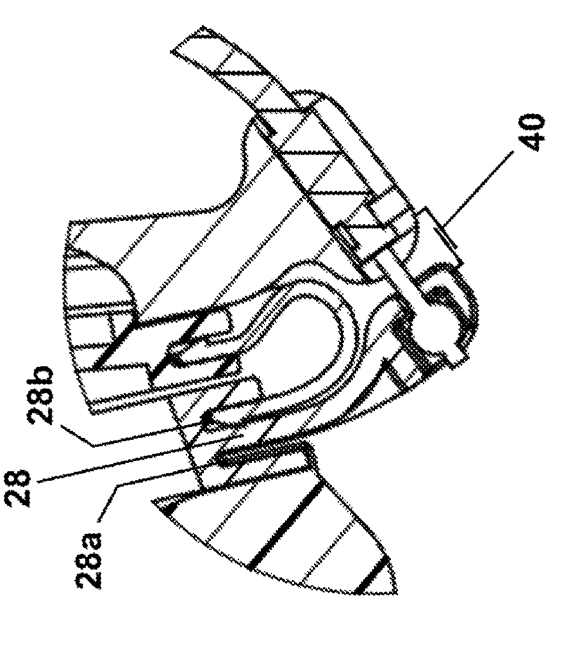

In order to solve this problem, the flexible element 26 may be folded at least in its lower part 26*a*, as may be seen best by comparing FIGS. 2 and 3, on the one side, and FIGS. 5 and 6, on the other side. As a consequence, at least the lower part of the ear pad 30 may be retracted towards the housing 22 (see FIG. 2), i.e. out of the way of the user's ear, when putting the helmet 10 on or taking it off, by transferring the flexible element 26 to its folded state. In order to provide the flexible element 26 with sufficient flexibility, it may be made, for example, from silicone, rubber or other types of flexible polymers.

As both, the flexible element 26 and the ear pad 30, due to their respective functions fail to provide sufficient dimensional stability in the radial direction, the stabilizing ring element 28 is arranged between the flexible element 26 and the ear pad 30. Accordingly, the stabilizing ring element 28 preferably is made from a rigid material, e.g. a thermoplastic material, for example, polycarbonate, ABS and the like, e.g. reinforced with fibers, preferably glass fibers.

Figure 4:
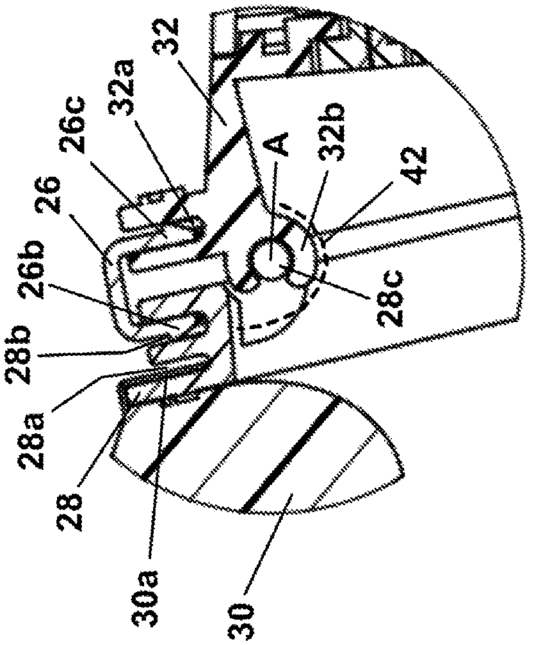
FIGS. 4 to 6 show enlarged views of details IV, V and VI of FIGS. 2 and 3.

As may be seen best from FIGS. 4 to 6, the stabilizing ring element 28 has two circumferential grooves 28*a* and 28*b* which are intended to receive a circumferential lip 30*a* of the ear pad 30 and a circumferential lip 26*b* of the flexible element 26, respectively. The circumferential grooves 28*a* and 28*b* preferably open in a radially outward direction, whereas the circumferential lips 30*a* and 26*b* preferably protrude in a radially inward direction from the ear pad 30 and the flexible element 26, respectively. Based on the cooperation of the two circumferential grooves 28*a* and 28*b* with the corresponding circumferential lips 26*b* and 30*a*, the stabilizing ring element 28 may be securely connected to the flexible element 26 and the ear pad 30. It goes without saying that other types of connection could be applied in addition or as an alternative, e.g. gluing.

As may be seen from FIGS. 2 and 3, the housing 22 may include a plurality of components, which will be described later. Here it is sufficient to note that the housing includes a main housing element 32.

The main housing element 32 has a circumferential groove 32*a*, preferably opening in a radially outward direction, which is intended to receive a circumferential lip 26*c* of the flexible element 26. Due to the cooperation of the circumferential groove 32*a* with the circumferential lip 26*c*, the flexible element 26 may be securely connected to the main housing element 32, and thus to the housing 22. It goes without saying that other types of connection could be applied in addition or as an alternative, e.g. gluing.

In order to enhance the reproducibility of the movement of the ear pad 30 relative to the housing 22 a pin element 28*c* integrally formed with the stabilizing ring element 28 and a socket element 32*b* integrally formed with the main housing element 32 and cooperating with the pin element 28*c* together form a hinge unit 28*c*/32*b* mechanically connecting the stabilizing ring element 28 to the main housing element 32 (see FIG. 4). Preferably, the hinge unit 28*c*/32*b* is provided at the upper end of the stabilizing ring element 28 and the main housing element 32. Furthermore, the axis A of the hinge unit 28*c*/32*b* preferably extends substantially parallel to a forward-backward direction of the user's head.

In order to control the movement of the ear pad 30 towards the housing 22, in other words the transfer of the flexible element 26 from its expanded state to its folded state, a Bowden cable-type activation mechanism 34 may be provided (see FIGS. 2 and 3).

The Bowden cable-type activation mechanism 34 comprises a Bowden-like cable 36 (see FIGS. 5 and 6) having an outer protective sheath 36*a* and an inner operating cable 36*b*. A connection element 36*a*1 fixed to the end 36*a*2 of the outer protective sheath 36*a* form-fittingly engages into a corresponding recess 38*a*1 of an abutment element 38*a* integrally formed with a lower cover element 38 of the housing 22. Furthermore, a ball-shaped element 36*b*1 attached to the inner operating cable 36*b* close to the free end thereof engages into a corresponding recess 28*d*1 of an abutment element 28*d* integrally formed with the stabilizing ring element 28. Thus, when pulling the inner operating cable 36*b*, cooperation of ball-shaped element 36*b*1 and abutment element 28*d* pulls the stabilizing ring element 28 and thus the ear pad 30 towards the housing 22 transferring the flexible element 26 to its folded state.

The ear pad 30 may be maintained in the retracted position by means of a latching mechanism (schematically indicated and denoted by reference numeral 40 in FIG. 5).

In order to avoid the necessity of separately operating the Bowden-like cable 36*b*, said Bowden-like cable 36*b* may be adapted to be connected to a chin strap (not shown) of the helmet 10. Thus, whenever the user pulls the helmet's chin straps, e.g. when putting the helmet 10 on or when loosening the chin straps connection for taking the helmet 10 off, the Bowden-like cables 36*b* move the ear pads 30 towards the respective housing 22 of the headphone units 20.

In order to enable the ear pad 30 to substantially automatically return to a position remote from the housing 22, i.e. a position in which it abuts against the user's head, a spring element (schematically indicated and denoted by reference numeral 42 in FIG. 4) may be provided for biasing said ear pad 30 away from said housing 22. And, in order to trigger this return movement, a button (schematically indicated and denoted by reference numeral 44 in FIG. 1) for releasing the latching mechanism 40 may be provided. This button may be located at any suitable position of the helmet 10.

It should be added here that, as is already known from prior art headphone units, an acoustic mesh 46 (see FIGS. 2 and 3) may be arranged between said stabilizing ring element 28 and said ear pad 30.

In order to allow access to the backside of the loudspeaker 24, e.g. for connecting a signal supply cable (not shown) to the loudspeaker 24, the housing 22 may comprise an upper cover element 48 which may be secured to the backside of the main housing element 32.

As a further improvement, the headphone unit 20 according to the present invention may be provided with active noise cancellation properties. To this end, at least one microphone 50 may be mounted to the main housing element 32 substantially in front of the loudspeaker 24 (see FIGS. 2 and 3). Furthermore, an additional microphone 52 may be provided in a space 54 enclosed by the main housing element 32 and the lower cover element 38. Finally, a further microphone (not shown) may be provided outside the headphone unit 20.

Similar to the stabilizing ring element 28, at least one of the element constituting the housing 22, namely the main housing element 32, the upper cover element 48 and the lower cover element, may be made from a rigid material, e.g. a thermoplastic material, for example, polycarbonate, ABS and the like, e.g. reinforced with fibers, preferably glass fibers.

Figure 7:
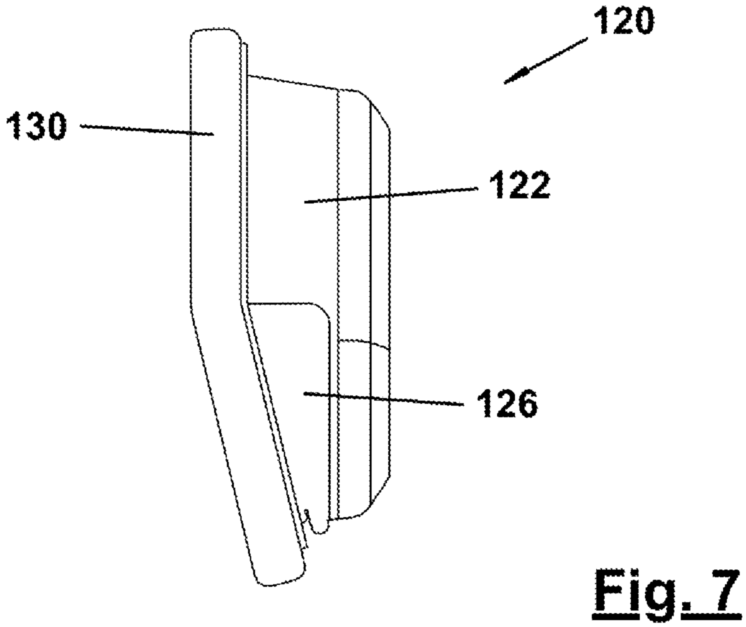
FIG. 7 shows a side view of a second embodiment of a headphone unit according to the invention.

FIGS. 7*a* and 7*b* show a second embodiment of a headphone unit 120 according to the present invention. The headphone unit 120 of FIGS. 7*a* and 7*b* differs from the headphone unit 20 of FIGS. 1 to 6 insofar as only the lower part of the ear pad 130 may be moved towards and away from the housing 122, and as the flexible element 126 which may be transferred between an expanded state (shown in FIG. 7*a*) and a folded state (shown in FIG. 7*b*) is provided only in the lower part of the headphone unit 120.

Figure 8:
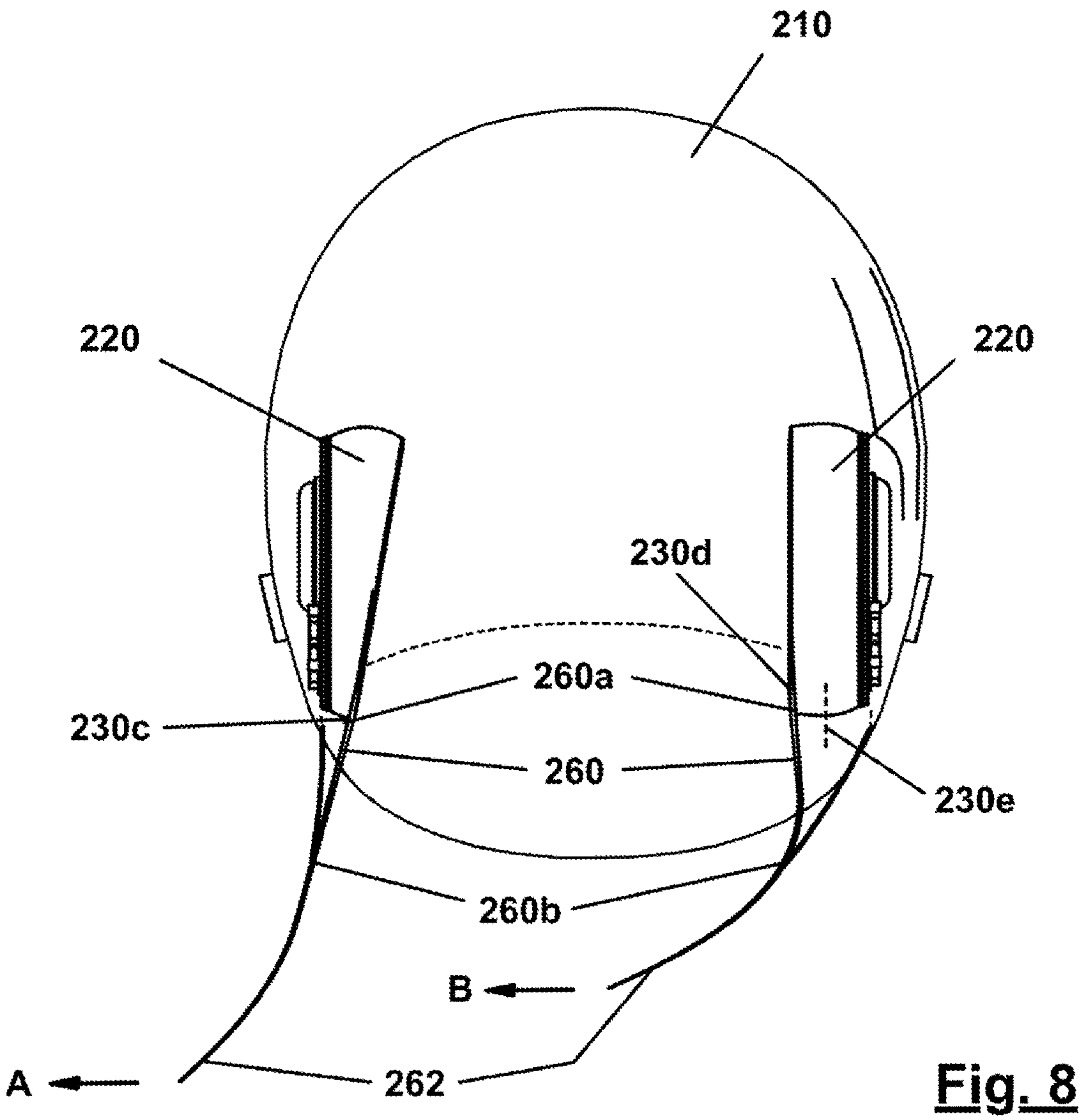
FIG. 8 shows a schematic view similar to FIG. 1 of a helmet including two headphone units according to a third embodiment of the invention.
Figure 9:
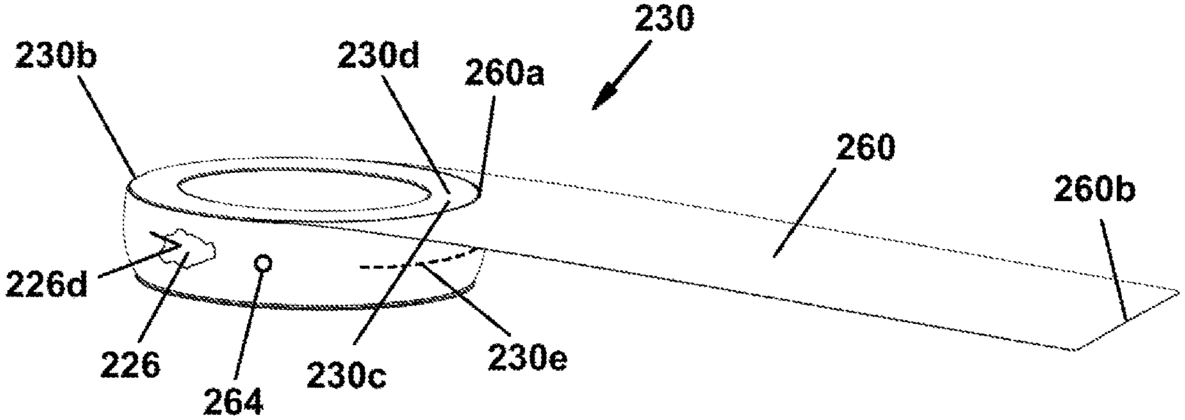
FIG. 9 shows a perspective view of an ear pad of the headphone units of FIG. 8.

FIGS. 8 and 9 show a third embodiment of a headphone unit 220 according to the present invention. The headphone unit 220 of FIGS. 8 and 9 differs from the headphone units 20 and 120 of the first and second embodiments insofar as the flexible element 226 may be integrated in the ear pad's main body 230*b* and as an elongate connection element 260 may be connected with its one longitudinal end 260*a* to a lower end 230*c* of the ear pad's main body 230*b*, while its respective other longitudinal end 260*b* may be connected to a chin strap 262 of the helmet 210.

When putting a helmet 210 on, the user of the helmet 210 usually grips the chin straps 262 of the helmet 210 and pulls both chin straps 262 sideways away from the head (see left side and arrow A in FIG. 8) or presses the chin straps sideways against the helmet, usually using the thumbs. As the ear pads 230 are connected to the chin straps 262 via the elongate connection elements 260, pulling the chin straps 262 sideways away from the head results in a compression of the flexible element 226 (to be seen in FIG. 9 in the partially broken away area of the surface of the ear pad's main body 230*b*) of the ear pad 230, thus allowing the helmet 210 to easily pass the user's ears. As soon as the user has put the helmet 210 on, he closes the chin straps 262 in order to secure the helmet 210 to her/his head.

To this end, the user pulls the chin straps towards each other (see right side and arrow B in FIG. 8), thus allowing or even causing a re-expansion of the compressed flexible elements 226 of the ear pads 230.

It goes without saying that analogous sideways movements of the chin straps 262 are also performed, when putting the helmet 210 off.

According to the invention, the flexible element 226 may be made from a compressible material, e.g. a compressible foam material. In order to allow the flexible element 226 to automatically return to its expanded state shown in FIG. 9, the flexible element 226 may be made from an elastically compressible material, e.g. an elastically compressible foam material. It is, however, also conceivable that the ear pad 230 is provided with means 264 (only schematically indicated in FIG. 9) for inflating the flexible element 226. In this context, it may be advantageous if the foam material is an open-pore foam material, preferably having a closed outer surface 226*d*.

In order to couple the elongate connection element 260 effectively to the lower part of the ear pad 230 so as to be able to compress the flexible element 226 over at least a predetermined length in circumferential direction of the ear pad 230, preferably over substantially the entire width of the ear pad 230, the elongate connection element 260 may be formed as a strip element. The width of the elongate connection element 260 may, for example, vary from the width of the ear pad 230 at its longitudinal end 260*a* to the width of the chin straps 262 at its other longitudinal end 260*b*.

According to FIGS. 8 and 9, the elongate connection element 260 is connected to the laterally inner side 230*d* of the ear pad's main body 230*b*, in order to provide an efficient compression of the flexible element 226. The elongate connection element 260 may, however, be connected to the ear pad's main body 230*b* as well at a certain distance from the laterally inner side 230*d*, namely for example at the position indicated in FIGS. 8 and 9 by a dashed line 230*e*.

The invention claimed is:

1. An earmuff unit for use within a head protective gear, wherein the head protective gear is separate from the earmuff unit, the earmuff unit comprising:

an ear pad; and a flexible element integrated in the ear pad and arranged in at least a lower portion of a circumference of the ear pad to allow the ear pad to move, in at least a part of the lower portion of the circumference, towards and away from a shell of the head protective gear, wherein the flexible element is made from compressible foam material.

2. The earmuff unit of claim 1, wherein the compressible foam material is elastically compressible.

3. The earmuff unit of claim 1, wherein one longitudinal end of an elongate connection element is connected to a lower end of the ear pad, wherein a respective other longitudinal end of the elongate connection element is adapted to be connected to a chin strap of the head protective gear.

4. The earmuff unit of claim 3, wherein the elongate connection element is connected to a laterally inner side of the ear pad.

5. The earmuff unit of claim 3, wherein the elongate connection element is elastically stretchable.

6. The earmuff unit of claim 3, wherein the elongate connection element comprises a strip element.

7. The earmuff unit of claim 1, wherein the earmuff unit comprises a housing.

8. The earmuff unit of claim 7, wherein the housing comprises a wedge-shaped design tapering towards a lower part of the housing.

9. The earmuff unit of claim 7, wherein the housing comprises at least one loudspeaker.

10. The earmuff unit of claim 9, further comprising at least one microphone.

11. The earmuff unit of claim 10, wherein the at least one microphone is located in front of the at least one loudspeaker.

12. The earmuff unit of claim 11, wherein an additional microphone is located behind or below the at least one loudspeaker.

13. The earmuff unit of claim 7, further comprising an acoustic mesh arranged between the housing and the ear pad.

14. The earmuff unit of claim 7, wherein the flexible element is arranged between the ear pad and the housing to allow the ear pad, in at least the part of the lower portion of the circumference of the ear pad, to move towards and away from the housing.

15. The earmuff unit of claim 14, further comprising a Bowden cable for one or more of moving the ear pad towards the shell or moving the ear pad away from the shell.

16. The earmuff unit of claim 14, further comprising a latching mechanism for holding the ear pad in a position moved towards the shell.

17. The earmuff unit of claim 16, further comprising a button for releasing the latching mechanism.

18. The earmuff unit of claim 14, further comprising a spring element for one or more of biasing the ear pad away from the shell or biasing the ear pad towards the shell.

19. The earmuff unit of claim 7, wherein, in an expanded state of the flexible element, the housing and the flexible element together form a bowl of uniform height over an entirety of the circumference of the ear pad.

20. The earmuff unit of claim 19, wherein a stabilizing ring element is mounted between the ear pad and the flexible element.

21. The earmuff unit of claim 20, wherein one or more of the housing and the stabilizing ring element is made from a rigid material.

22. The earmuff unit of claim 20, wherein one or more of the housing and the stabilizing ring element has a circumferential groove intended to cooperate with a mating circumferential lip of the flexible element.

23. The earmuff unit of claim 1, wherein the flexible element extends over the circumference of the ear pad.

24. The earmuff unit of claim 1, further comprising an inflation unit configured to inflate the flexible element of the ear pad.

25. A head protective gear comprising:

an outer shell;

an inner padding; and at least one earmuff unit mounted in an allocated recess of the inner padding, the at least one earmuff unit comprising:

a housing;

an ear pad;

a flexible element arranged in at least a lower portion of a circumference of the ear pad between the ear pad and the housing to allow the ear pad to move, in at least a part of the lower portion of the circumference, towards and away from the housing and the outer shell; and a latching mechanism for holding the ear pad in a position moved towards the outer shell.

26. The head protective gear of claim 25, further comprising at least one microphone located outside the head protective gear.

27. A head protective gear comprising:

an outer shell;

an inner padding and at least one earmuff unit mounted in an allocated recess of the inner padding, the at least one earmuff unit comprising:

a housing, an ear pad, a flexible element arranged in at least a lower portion of a circumference of the ear pad between the ear pad and the housing to allow the ear pad to move, in at least a part of the lower portion of the circumference, towards and away from the housing and the outer shell; and a Bowden cable for retracting the at least one earmuff unit towards the outer shell, wherein the Bowden cable is configured to be connected to a chin strap of the head protective gear.

28. An earmuff unit for use within a head protective gear, wherein the head protective gear is separate from the earmuff unit, the earmuff unit comprising:

an ear pad;

a flexible element arranged in at least a lower portion of a circumference of the ear pad to allow the ear pad to move, in at least a part of the lower portion of the circumference, towards and away from a shell of the head protective gear;

a housing, wherein, in an expanded state of the flexible element, the housing and the flexible element together form a bowl of uniform height over an entirety of the circumference of the ear pad; and a stabilizing ring element mounted between the ear pad and the flexible element and pivotably connected to the housing in a pivotable connection.

29. The earmuff unit of claim 28, wherein the pivotable connection is provided at an upper portion of the earmuff unit.

30. The earmuff unit of claim 28, wherein the pivotable connection is provided by a hinge unit having a hinge axis.

31. An earmuff unit for use within a head protective gear, wherein the head protective gear is separate from the earmuff unit, the earmuff unit comprising:

a housing;

an ear pad;

a flexible element arranged in at least a lower portion of a circumference of the ear pad between the ear pad and the housing to allow the ear pad to move, in at least a part of the lower portion of the circumference, towards and away from the housing and a shell of the head protective gear; and a latching mechanism for holding the ear pad in a position moved towards the shell.

* * * * *